US008457763B2

(12) United States Patent
Gerber et al.

(10) Patent No.: US 8,457,763 B2
(45) Date of Patent: Jun. 4, 2013

(54) IMPLANTABLE MEDICAL ELECTRICAL STIMULATION LEAD FIXATION METHOD AND APPARATUS

(75) Inventors: Martin T. Gerber, Maple Grove, MN (US); Eric H. Bonde, Minnetonka, MN (US)

(73) Assignee: Medtronic, Inc., Minneapolis, MA (US)

( * ) Notice: Subject to any disclaimer, the term of this patent is extended or adjusted under 35 U.S.C. 154(b) by 1114 days.

(21) Appl. No.: 11/380,458

(22) Filed: Apr. 27, 2006

(65) Prior Publication Data
US 2007/0255364 A1 Nov. 1, 2007

(51) Int. Cl.
*A61N 1/00* (2006.01)

(52) U.S. Cl.
USPC ............... 607/117; 607/115; 607/122

(58) Field of Classification Search
USPC .................. 607/115, 117, 122, 126
See application file for complete search history.

(56) References Cited

U.S. PATENT DOCUMENTS

| 5,304,219 | A | * | 4/1994 | Chernoff et al. ............ 607/122 |
| 5,484,445 | A | | 1/1996 | Knuth |
| 5,876,431 | A | * | 3/1999 | Spehr et al. ............... 607/126 |
| 5,957,965 | A | | 9/1999 | Moumane et al. |
| 5,957,966 | A | * | 9/1999 | Schroeppel et al. ........ 607/122 |
| 6,083,216 | A | * | 7/2000 | Fischer, Sr. .................. 604/530 |
| 6,104,960 | A | | 8/2000 | Duysens et al. |
| 6,388,043 | B1 | | 5/2002 | Langer et al. |
| 6,430,449 | B1 | * | 8/2002 | Hsu et al. ................... 607/126 |
| 6,720,402 | B2 | | 4/2004 | Langer et al. |
| 6,972,016 | B2 | * | 12/2005 | Hill et al. ..................... 606/41 |
| 6,999,819 | B2 | | 2/2006 | Swoyer et al. |
| 7,177,702 | B2 | * | 2/2007 | Wallace et al. .............. 607/117 |
| 2003/0050681 | A1 | * | 3/2003 | Pianca et al. ................. 607/125 |
| 2003/0105501 | A1 | * | 6/2003 | Warman et al. .............. 607/27 |
| 2003/0195603 | A1 | * | 10/2003 | Scheiner et al. ............ 607/122 |
| 2005/0060014 | A1 | * | 3/2005 | Swoyer et al. ............... 607/117 |
| 2005/0203602 | A1 | * | 9/2005 | Wallace et al. .............. 607/122 |
| 2005/0288781 | A1 | | 12/2005 | Moaddeb et al. |
| 2006/0041089 | A1 | | 2/2006 | Mather et al. |

FOREIGN PATENT DOCUMENTS

CA 2527976 A1 7/2006

OTHER PUBLICATIONS

Lendlein, "Shape Memory Polymers—Biodegradable Sutures", Abstracted from Materials World, Jul. 2002, 10:7, p. 29-30, Website Article: www.azom.com/details.asp?articleID=1542.
Wingfield, "Shape Change Materials", Feb. 2006: 13:08, Website Article: www.loop.ph/twiki/bin/view/Openloop/ShapeChange.

* cited by examiner

Primary Examiner — Nicole F Lavert

(57) ABSTRACT

The invention includes an implantable medical electrical lead for electrical stimulation of body tissue that includes at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and at least one electrode configured to provide electrical stimulation of body tissue, wherein the lead has a proximal end and a distal end. Systems including leads of the invention and methods of implanting leads of the invention are also included.

41 Claims, 11 Drawing Sheets

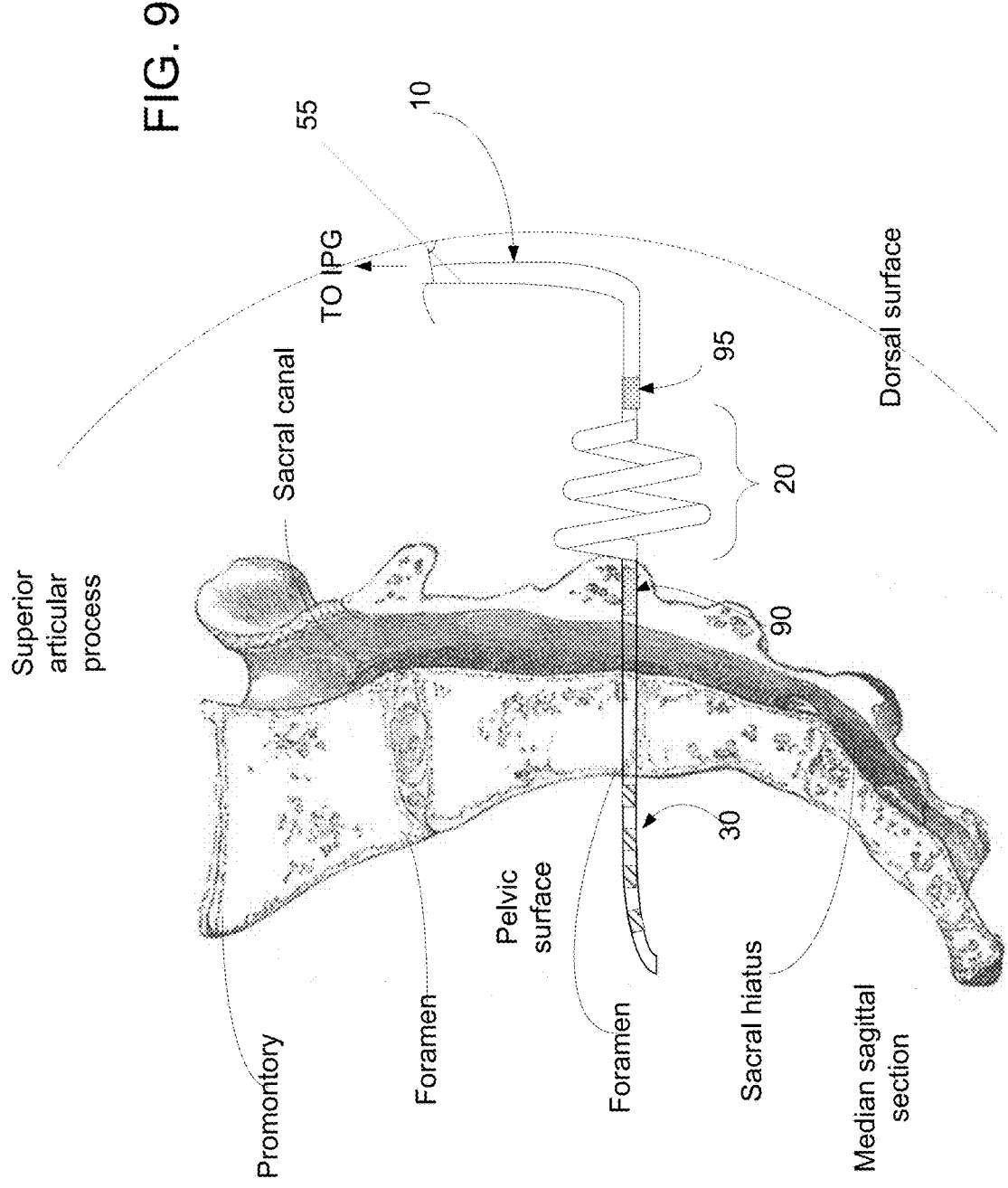

IMPLANTABLE MEDICAL ELECTRICAL STIMULATION LEAD FIXATION METHOD AND APPARATUS

FIELD OF THE INVENTION

This invention relates generally to device for electrical stimulation of body tissue. More specifically, this invention relates to an implantable medical electrical lead having at least one stimulation electrode and a fixation mechanism for fixing the lead within the tissue.

BACKGROUND OF THE INVENTION

Pelvic floor disorders such as, urinary incontinence, urinary urge/frequency, urinary retention, pelvic pain, bowel dysfunction (constipation, diarrhea), and erectile dysfunction, involve bodily functions that are influenced by the sacral nerves. Specifically, urinary incontinence is the involuntary control over the bladder that is exhibited in various patients. Urinary incontinence is primarily treated through pharmaceuticals and surgery. Many of the pharmaceuticals do not adequately resolve the issue and can cause unwanted side effects, and a number of the surgical procedures have a low success rate and are not reversible. Several other methods have been used to control urinary incontinence, for example, vesicostomy or an artificial sphincter implanted around the urethra. These solutions have drawbacks well known to those skilled in the art. In addition, the other mentioned disorders do not have adequate pharmaceutical or surgical treatment options.

The organs involved in bladder, bowel, and sexual function receive much of their control via the sacral nerves, in some instances the second, third, and fourth sacral nerves, commonly referred to as S2, S3 and S4 respectively. Electrical stimulation of these various nerves has been found to offer some control over these functions.

Neurostimulation leads with at least one stimulation electrode positioned on or near the sacral nerves of the human body have been implanted to provide partial control for urinary incontinence. Temporary sacral nerve stimulation is accomplished through implantation of a temporary neurostimulation lead extending through the skin and connected with a temporary external pulse generator as described for example in commonly assigned U.S. Pat. Nos. 5,957,965 and 6,104,960. A permanent neurostimulator can be implanted if the temporary stimulation is efficacious and it is possible to do so in the particular patient. Permanent implantation can be accomplished by implanting a permanent neurostimulation lead, extending the proximal portion of the lead body subcutaneously, and connecting its proximal end with an implantable pulse generator (IPG) implanted subcutaneously.

One problem that can be associated with implantation of both permanent and temporary neurostimulation leads involves maintaining the electrode(s) in casual contact, that is in a location where slight contact of the electrode with the sacral nerve may occur or in close proximity to the sacral nerve to provide adequate stimulation of the sacral nerve, while allowing for some axial movement of the lead body. In order to minimize the movement of the lead, the lead body is fixed to retard migration and dislodgement of the electrodes from the optimal position. This can be accomplished by employing sutures or a sacral lead fixation mechanism, an example of which is described in commonly assigned U.S. Pat. No. 5,484,445. An example of a lead that includes a fixation mechanism can be found in commonly assigned U.S. Pat. No. 6,999,819, the disclosure of which is incorporated herein by reference. Although the fixation mechanisms of the above referenced patents are a significant advance over the prior art, there are still further advantages to be gained. For example, it can be difficult to place those leads because once the tines are released from the dilator sheath, the tines deploy and it becomes impossible to retract the lead body and position it again. Therefore, there remains a need for a lead having a fixation mechanism that can be easily repositioned.

SUMMARY OF THE INVENTION

The invention includes an implantable medical electrical lead for electrical stimulation of body tissue that includes at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and at least one electrode configured to provide electrical stimulation of body tissue, wherein the lead has a proximal end and a distal end.

The invention also includes a medical electrical stimulation system that includes an implantable pulse generator for providing medical electrical stimulation; and a medical electrical lead coupled to the implantable pulse generator for electrical stimulation of body tissue, the medical electrical lead including at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and at least one electrode configured to provide electrical stimulation of body tissue, wherein the lead has a proximal end and a distal end.

The invention further includes a method of providing electrical stimulation of body tissue at a stimulation site employing an implantable pulse generator that includes providing an implantable medical lead having a lead body extending between lead proximal and distal ends; at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and at least one electrode configured to provide electrical stimulation of body tissue; at least one proximal connector element formed in a connector array in a proximal segment of the lead body; percutaneously introducing the implantable medical lead adjacent to the stimulation site; exposing at least the modifiable portion of the lead to the temperature of the body tissue; and coupling the at least one proximal connector element with the implantable pulse generator.

The full range of advantages and features of this invention are only appreciated by a full reading of this specification and a full understanding of the invention. Therefore, to complete this specification, a detailed description of the invention and the preferred embodiments follow, after a brief description of the drawings, wherein additional advantages and features of the invention are disclosed.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Embodiments of the invention are illustrated in the drawings, wherein like reference numerals refer to like elements in the various views. Furthermore, it will be understood by one of skill in the art that the drawings are not drawn to scale.

FIG. 9 is a cross-section view of the sacrum schematically illustrating a further step of implanting a lead of the invention subcutaneously routing the proximal portion of the lead body to the implantation site of the neurostimulator IPG.

DETAILED DESCRIPTION OF THE INVENTION

A lead in accordance with the invention can be utilized to provide neurostimulation or neuromodulation to any portion of the nervous system within the body of a patient. In one embodiment a lead in accordance with the invention can be utilized in any target tissue that requires some amount of fixation or traction to minimize movement of the lead. In one embodiment the lead can be implanted within muscle or connective tissue to stimulate or modulate peripheral nerves within that tissue.

A lead in accordance with the invention can be placed anywhere within the body where electrical stimulation is desired. In one embodiment a lead in accordance with the invention can be utilized to provide neurostimulation within the pelvic region of a patient. In such an embodiment the lead may be positioned to provide stimulation to one or more of the sacral nerves. Sacral nerves that may be stimulated using a lead in accordance with the invention include, but are not limited to the pudendal nerve, the pelvic splanchnic nerve, the cavernosa nerve in the penis or nerves located in or near the clitoris in a female, the hypogastric nerve, the vesicle nerve plexus, the perineal nerves, the pelvic nerve plexus, the prostate gland, the prostatic plexus nerve, the vagina, the anus, the urethra, the penis dorsal nerve, the inferior rectal nerves, the scrotal nerves, scrotum, Alcock's Canal, the sacro-tuberous ligament, the ischial tuberosity, the greater sciatic foramen, the lesser sciatic foramen, and other nerves or nerve portions located in the general region of the pelvic floor.

Neurostimulation using a lead in accordance with the invention can be utilized to treat any of a number of conditions including, but not limited to pelvic floor disorders such as urinary control disorders, fecal control disorders, sexual dysfunction, pelvic pain, interstitial cystitis, endometriosis, and genital pain such as vulvodynia or idiopathic chronic testicular pain. Although the invention is discussed with respect to stimulation of one or more nerves within the pelvic floor for the treatment of urinary incontinence, it will be understood by one of skill in the art, that leads of the invention can be utilized to treat other disorders or conditions by stimulating other nerves.

In one embodiment, a lead in accordance with the invention can be used with a therapy for treating urinary incontinence, such as MEDTRONIC INTERSTIM® Therapy. For example, an implantable neurostimulation system may stimulate organs involved in urinary, fecal or sexual function via C-fibers or sacral nerves at the second, third, and fourth sacral nerve positions, commonly referred to as S2, S3, and S4, respectively. In another embodiment a lead in accordance with the invention can be used with a therapy for treating gastroparesis, such as MEDTRONIC ENTERRA® Therapy.

Figure 1A:
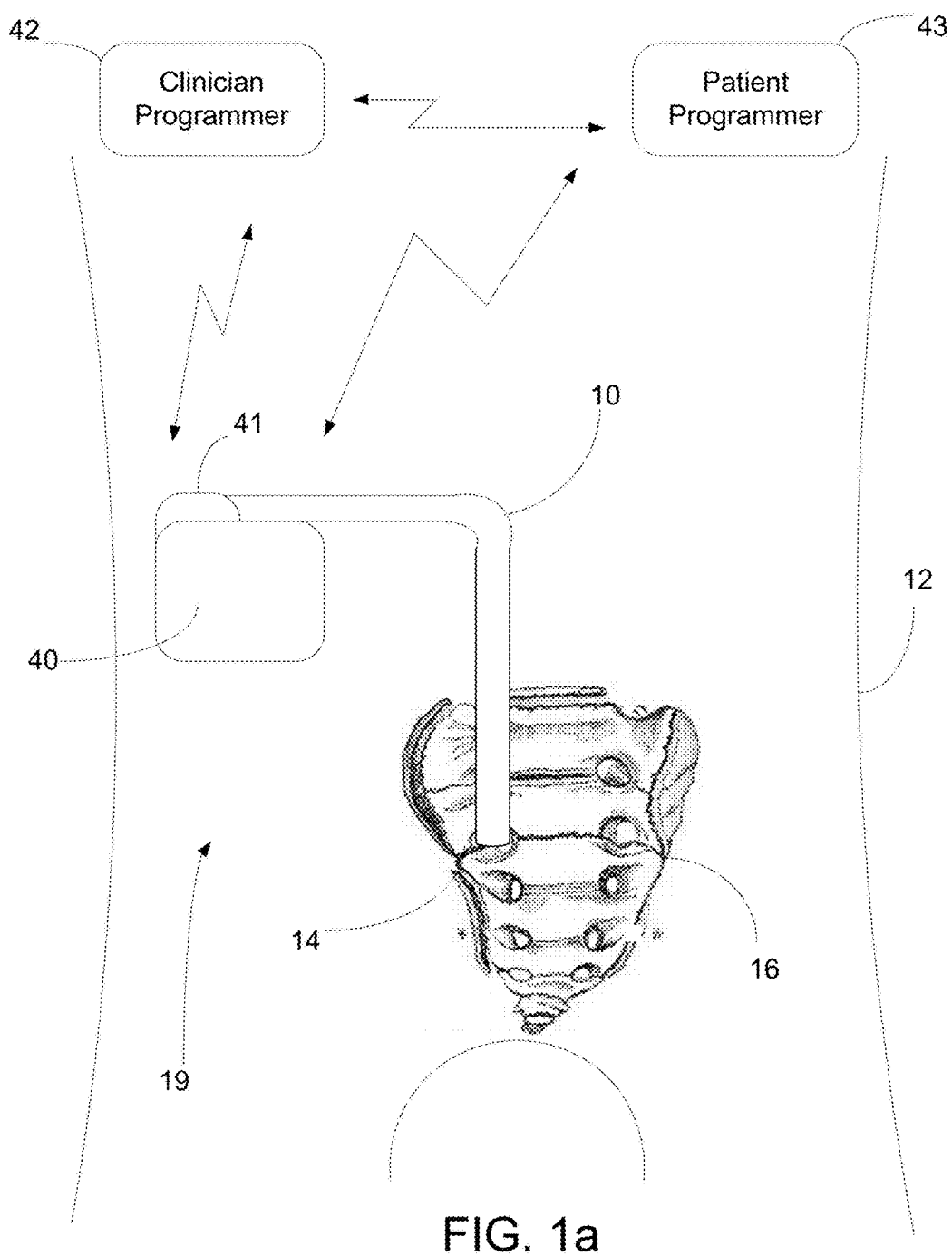
FIG. 1A is a diagram illustrating an implantable neurostimulator system for stimulating nerves, such as sacral nerves via a lead.

FIG. 1A is a diagram illustrating an implantable neurostimulation system 19 for stimulating a nerve, such as a sacral nerve, via lead 10. Lead 10 is generically depicted in FIG. 1A, and does not necessarily depict all of the features of a lead in accordance with the invention. Neurostimulation system 19 delivers neurostimulation to the sacral nerves or other regions of the nervous system known to treat pelvic floor disorders, urinary control disorders, fecal control disorders, interstitial cystitis, sexual dysfunction, and pelvic pain. Again, neurostimulation system 19 and lead 10 may be useful in other neurostimulation applications, such as spinal cord stimulation, deep brain stimulation, gastric stimulation, and the like. As shown in FIG. 1A, system 19 includes lead 10 and an implantable neurostimulator 40. In addition, a proximal end 32 of stimulation lead 10 may be coupled to a connector block 41 associated with neurostimulator 40.

Neurostimulator 40 includes an implantable pulse generator, and delivers neurostimulation therapy to patient 12 in the form of electrical pulses generated by the implantable pulse generator. In the example of FIG. 1A, neurostimulator 40 is implanted in the upper left buttock of patient 12, but may be implanted at other locations. An example of a commercially available neurostimulator includes, but is not limited to MEDTRONIC® Model 3023 Neurostimulator.

Lead 10 carries one or more stimulation electrodes, for example, 1 to 8 electrodes, to permit delivery of electrical stimulation to sacral nerves. Embodiments of the invention may have 1, 2, 3, 4, 5, 6, 7, 8 or more electrodes. The at least one electrode 30 can include ring electrodes, coil electrodes, circumferential segment electrodes, or any combination thereof. One embodiment of a lead in accordance with the invention has at least two (2) electrodes. Another embodiment of a lead in accordance with the invention has at least four (4) electrodes. In one embodiment having at least four electrodes, at least one of those electrodes can be a coil electrode. In another embodiment of the invention having at least four electrodes, at least one electrode is a coil electrode and at least one of the other electrodes is a ring electrode.

The at least one electrode 30 can be made of any commonly utilized material as is known to those of skill in the art. In one embodiment the at least one electrode 30 is made of a solid surface, bio-compatible material, examples of such materials include, but are not limited to, platinum, a platinum-iridium alloy, or stainless steel for example. Also, in some embodiments, lead 10 may carry one or more electrodes capable of sensing one or more parameters to permit neurostimulator 40 to sense electrical signals within sacrum 16, for example. In some embodiments, neurostimulator 40 may be coupled to two or more leads deployed at different positions, for example, relative to the spinal cord or sacral nerves.

In one embodiment lead 10 includes an outer lead body defining an inner lumen that contains one or more conductors to electrically couple the one or more electrodes to terminals within neurostimulator 40. In one embodiment the lead body outer diameter can be from about 0.5 mm to about 2 mm. In yet another embodiment, the lead body outer diameter is about 1 mm to about 1.5 mm. In a further embodiment the lead body outer diameter is about 1.3 mm.

Leads in accordance with the invention can have variable lengths, depending at least in part on considerations such as the type of tissue that the lead is to be implanted in, the surrounding anatomy where the lead will be implanted, the particular configuration of the lead, the number of modifiable portions within the lead, the number of electrodes within the lead, the location of the one or more modifiable portions and/or the one or more electrodes within the lead, whether or not the lead will be used with an extension, and where the neurostimulator is to be implanted, for example.

In one embodiment of the invention, where the lead is to be used for stimulation of the pelvic floor with a lead extension, the length of the lead can range from about 10 cm to about 100 cm. In another embodiment of the invention, where the lead is to be used for stimulation of the pelvic floor with a lead extension, the length of the lead can range from about 10 cm to about 80 cm. In yet another embodiment of the invention, where the lead is to be used for stimulation of the pelvic floor with a lead extension, the length of the lead can range from about 20 cm to about 60 cm.

Figure 1B:
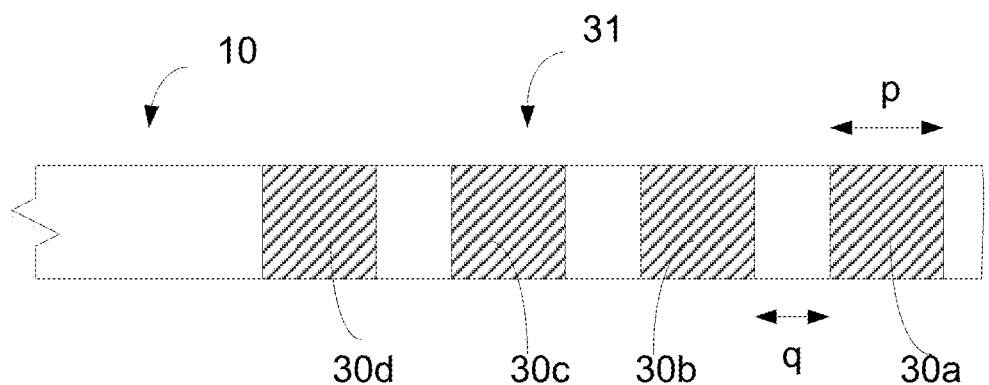
FIG. 1B is a diagram illustrating a portion of a lead in accordance with the invention.
Figure 1C:
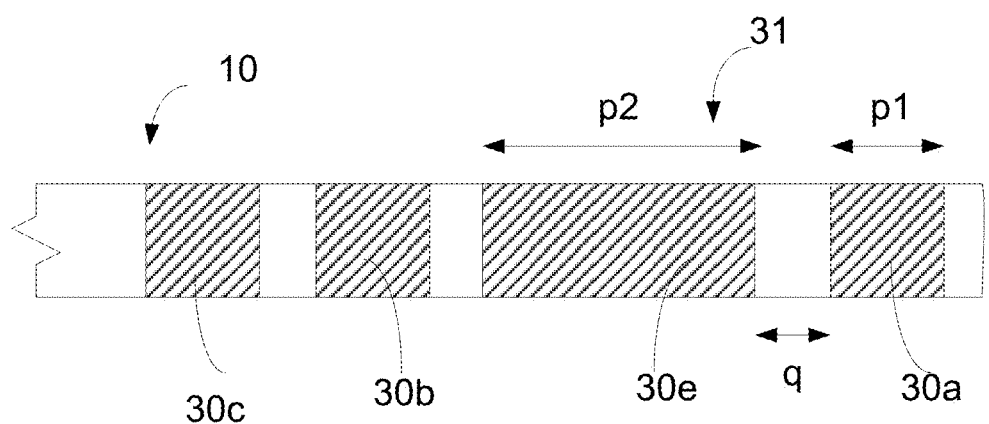
FIG. 1C is a diagram illustrating a portion of a lead in accordance with the invention.

In one embodiment, the at least one electrode 30 is located towards the distal end 31 of the lead 10. FIG. 1B depicts a portion of an exemplary lead 10 in accordance with the invention. The exemplary lead 10 depicted there includes four electrodes 30a, 30b, 30c, and 30d. The electrodes 30a, 30b, 30c, and 30d have an electrode length p. In this example, the four electrodes 30a, 30b, 30c, and 30d have equal electrode lengths p. One of skill in the art, having read this specification, will understand that the electrode lengths p could be different or the same. One of skill in the art will also understand that the electrode lengths p of any one electrode or all of the electrodes can vary and may be at least in part dependent on a number of factors including, but not limited to, the type of tissue that the lead will be implanted in, the surrounding anatomy where the lead will be implanted, the stimulation parameters that the lead will be delivering, the types of electrodes, and the number of electrodes.

In one embodiment, the electrode length p can range from about 1 mm to about 20 mm. In another embodiment the electrode length p can range from about 1 mm to about 3 mm. In yet another embodiment the electrode length p can range from about 3 mm to about 10 mm. In one embodiment, a lead 10 has at least one electrode that has an electrode length p of about 3 mm. In another embodiment, a lead 10 has at least one electrode that has an electrode length p of about 10 mm.

The electrodes 30a, 30b, 30c, and 30d are separated by inter-electrode distances q. In this example, the four electrodes 30a, 30b, 30c, and 30d are separated by equal inter-electrode distances q, but one of skill in the art, having read this specification, will understand that the inter-electrode distances q could be different. One of skill in the art, having read this specification, will also understand that the inter-electrode distances q of any one electrode or all of the electrodes can vary and may be at least in part dependent on a number of factors including, but not limited to the type of tissue that the lead will be implanted in, the surrounding anatomy where the lead will be implanted, the stimulation parameters that the lead will be delivering, the types of electrodes, and the number of electrodes.

In one embodiment, the inter-electrode distances q can range from about 0.5 mm to about 5 mm. In another embodiment the inter-electrode distances q can range from about 1 mm to about 2 mm. In yet another embodiment the inter-electrode distances q can range from about 1.2 mm to about 1.6 mm. In one embodiment, a lead 10 has at least two electrodes that have an inter-electrode distance q of about 1.5 mm. In another embodiment, a lead 10 has at least two electrodes that have an inter-electrode distance q of about 3 mm.

The exemplary lead depicted in FIG. IC also includes four electrodes 30a, 30b, 30c, and 30e in which only three of the electrodes 30a, 30b, and 30c have the same electrode lengths $p_1$, and the fourth electrode 30e has a different electrode length $p_2$. One of skill in the art, having read this specification, will understand that any combination of equal and unequal electrode lengths $p_1$-$p_2$ are included within the scope of this invention. In one embodiment of the invention, a lead includes four ring electrodes with the same electrode lengths p. In another embodiment of the invention, a lead includes three ring electrodes with the same electrode lengths p and one coil electrode with a different electrode length p.

The at least one electrode can be electrically coupled to the distal end of a coiled wire lead conductor within the body of the lead. The proximal ends of the separately insulated lead conductors can each be coupled to respective connector elements, for example ring-shaped connector elements, in a proximal connector element array in the body of the lead. In one embodiment, the conductor wires can be formed of an MP35N alloy and are insulated from one another within an insulating polymer sheath such as polyurethane, fluoropolymer or silicone rubber for example. The lead conductor wires can be separately insulated by an insulation coating and can be wound in a quadra-filar manner having a common winding diameter within the outer sheath. The coil formed by the coiled wire conductors defines a lead body lumen of the lead body. It will be understood that a further inner tubular sheath could be interposed within the aligned wire coils to provide the lead body lumen.

The connector elements can be adapted to be coupled with a neurostimulator IPG, additional intermediate wiring, or other stimulation device adapted to be implanted subcutaneously. An example of such an implantable pulse generator is the MEDTRONIC® Neurostimulator Model 3023. Electrical stimulation pulses generated by the neurostimulator IPG are applied to a nerve or nerves, such as the sacral nerve, through the at least one electrode in either a unipolar or bipolar stimulation mode.

As further shown in FIG. 1A, implantable neurostimulation system 19 also may include a clinician programmer 42 and a patient programmer 43. Clinician programmer 42 may be a handheld computing device that permits a clinician to program neurostimulation therapy for patient 12, e.g., using input keys and a display. For example, using clinician programmer 42, the clinician may specify neurostimulation parameters for use in delivery of neurostimulation therapy.

Clinician programmer 42 supports radio frequency telemetry with neurostimulator 40 to download neurostimulation parameters and, optionally, upload operational or physiological data stored by neurostimulator. In this manner, the clinician may periodically interrogate neurostimulator 40 to evaluate efficacy and, if necessary, modify the stimulation parameters.

Like clinician programmer 42, patient programmer 43 may be a handheld computing device. Patient programmer 43 may also include a display and input keys to allow patient 12 to interact with patient programmer 43 and implantable neurostimulator 40. In this manner, patient programmer 43 provides patient 12 with an interface for control of neurostimulation therapy by neurostimulator 40.

For example, patient 12 may use patient programmer 43 to start, stop or adjust neurostimulation therapy. In particular, patient programmer 43 may permit patient 12 to adjust stimulation parameters such as duration, amplitude, pulse width and pulse rate, within an adjustment range specified by the clinician via clinician programmer 42.

Neurostimulator 40, clinician programmer 42 and patient programmer 43 may communicate via wireless communication, as shown in FIG. 1A. Clinician programmer 42 and patient programmer 43 may, for example, communicate via wireless communication with neurostimulator 40 using RF telemetry techniques known in the art. Clinician programmer 42 and patient programmer 43 also may communicate with each other using any of a variety of local wireless communication techniques, such as RF communication according to the 802.11 or Bluetooth specification sets, or other standard or proprietary telemetry protocols.

Figure 1D:
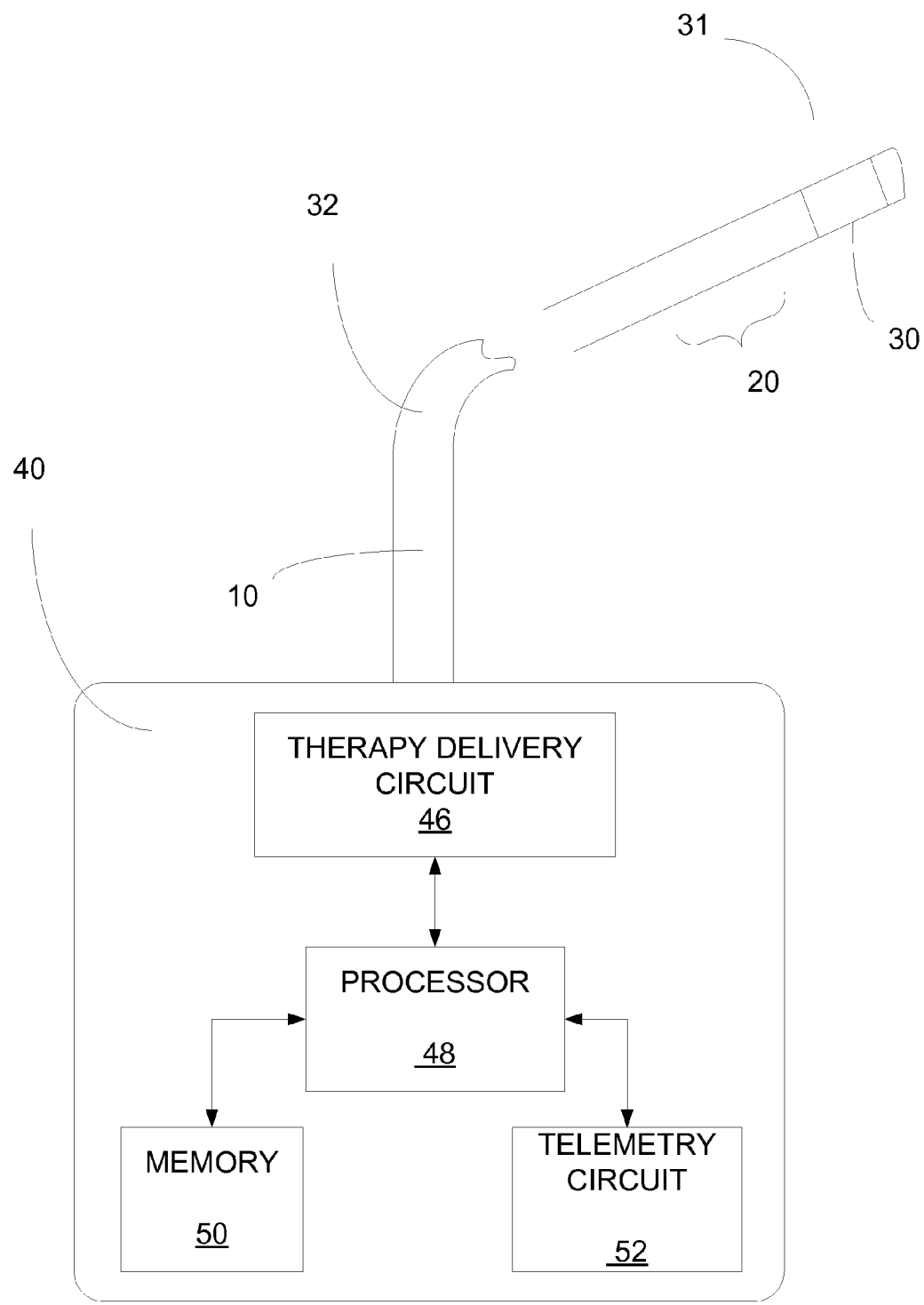
FIG. 1D is a block diagram illustrating various components of an implantable neurostimulator with an implantable lead incorporating a fixation mechanism.

FIG. 1D is a block diagram illustrating various components of an implantable neurostimulator 40 incorporating an implantable lead 10 with a modifiable portion 20. As shown in FIG. 1D, neurostimulator 40 delivers neurostimulation therapy via at least one electrode 30 of lead 10. Electrode 30 is electrically coupled to a therapy delivery circuit 46 via conductors within lead 10. Therapy delivery circuit 46 may, for example, include an implantable pulse generator coupled to a power source such as a battery. The implantable pulse generator within therapy delivery circuit 46 delivers electrical pulses to patient 12 via the at least one electrode 30 under the control of a processor 48.

Processor 48 controls the implantable pulse generator within therapy delivery circuit 46 to deliver neurostimulation therapy according to selected stimulation parameters. In one embodiment, processor 48 can control therapy delivery circuit 46 to deliver electrical pulses with selected amplitudes, pulse widths, rates, or some combination thereof as specified by the program(s). In addition, processor 48 can also control therapy delivery circuit 46 to deliver the neurostimulation pulses via selected subsets of one or more electrodes 30 with selected polarities.

Processor 48 may control therapy delivery circuit 46 to deliver each pulse according to a different program, thereby interleaving programs to simultaneously treat different symptoms or provide a combined therapeutic effect. For example, in addition to treatment of one symptom such as sexual dysfunction, neurostimulator 40 may be configured to deliver neurostimulation therapy to treat other symptoms such as pain or incontinence. Processor 48 may include a microprocessor, a controller, a digital signal processor (DSP), an application-specific integrated chip (ASIC), a field-programmable gate array (FPGA), discrete logic circuitry, or the like.

Neurostimulator 40 also includes a memory 50. In some embodiments, memory 50 stores multiple sets of stimulation parameters that are available to be selected by patient 12 for delivery of neurostimulation therapy to the patient 12. For example, memory 50 may store stimulation parameters transmitted by clinician programmer 42.

Memory 50 also stores program instructions that, when executed by processor 48, cause neurostimulator 40 to deliver neurostimulation therapy. Memory 50 may include any volatile or non-volatile media, such as random access memory (RAM), random read-only memory (ROM), compact disc-read-only memory (CD-ROM), non-volatile random access memory (NVRAM), electrically erasable programmable read-only memory (EEPROM), flash memory, and the like. Accordingly, computer-readable media storing instructions may be provided to cause processor 48 to provide functionality as described herein.

In some embodiments a telemetry circuit 52 can support wireless communication between two or more of neurostimulator 40, clinician programmer 42, and patient programmer 43. In addition, in some embodiments, telemetry circuit 52 supports wireless communication with one or more wireless sensors that sense physiological signals and transmit the signals to neurostimulator 40 clinician programmer 42, patient programmer 43 or some combination thereof.

As mentioned above, migration of lead 10 can have detrimental effects on the efficacy of neurostimulation therapy for a patient 12. Fixing the neurostimulation lead 10 to surrounding tissue may prevent harmful effects that may result from a loose neurostimulation lead 10. As described below, a lead in accordance with the invention may provide fixation (not shown in FIGS. 1A through 1D) between the lead 10 and tissue surrounding the lead 10, such as tissue within the sacrum 16, without the need for surgical implantation techniques, such as sutures.

Leads in accordance with the invention can be utilized for electrical stimulation of body tissue and include at least one modifiable portion that exhibits a first configuration when exposed to a first temperature and a second configuration when exposed to a second temperature, wherein the second temperature is higher than the first temperature and wherein the second configuration of the modifiable portion exhibits a greater resistance to movement of the lead within the body tissue than does the first configuration, and at least one electrode configured to provide electrical stimulation of body tissue.

Leads of the invention include at least one modifiable portion. As used herein, a modifiable portion is a portion of the lead that is capable of having at least two different configurations, a first configuration when exposed to a first temperature and a second configuration when exposed to a second temperature. The second configuration exhibits a greater resistance to movement of the lead within the body tissue than does the first configuration. For example, the first configuration could be straight and the second configuration could be a helix.

In one embodiment, the modifiable portion of the lead is made of a shape memory alloy or a superelastic material. A shape memory alloy (SMA), which is also referred to as a memory metal or smart wire is generally a metal that remembers its geometry, in that after it is deformed, it regains its original geometry through exposure to a higher temperature. The higher temperature phase is known as the martensitic phase, and the lower temperature phase is known as the austenitic phase. The temperature at which the transition occurs is generally called the transition temperature.

Examples of SMAs include, but are not limited to copper-zinc-aluminum alloys, copper-aluminum-nickel alloys, and nickel-titanium alloys. Nickel-titanium SMAs are also referred to as Nitinol. Generally the transition temperature of a Nitinol alloy can be tuned by varying the ratios of the nickel and titanium.

In one embodiment a SMA with a transition temperature between about 20 degrees Celsius and about 40 degrees Celsius is utilized. In another embodiment a SMA with a transition temperature between about 25 degrees Celsius and about 37 degrees Celsius is utilized. In yet another embodiment a SMA with a transition temperature between about 30 degrees Celsius and about 37 degrees Celsius is utilized. In a further embodiment a SMA with a transition temperature of about 30 degrees Celsius is utilized.

In one embodiment of the invention, a Nitinol alloy grade B, or BD that has a transition temperature around an average body temperature can be used. One specific example of an alloy that can be used includes a Nitinol alloy of about 55% to about 56% nickel and about 44% to about 45% titanium. Another specific example of an alloy that can be used includes a Nitinol alloy of about 56% nickel and about 44% titanium. Yet another specific example of an alloy that can be used includes a Nitinol ally of about 55.7% nickel and 44.3% titanium. Alloys such as those exemplified are in the martensite phase at room temperature and in the austenite phase at body temperature.

Figure 2A:
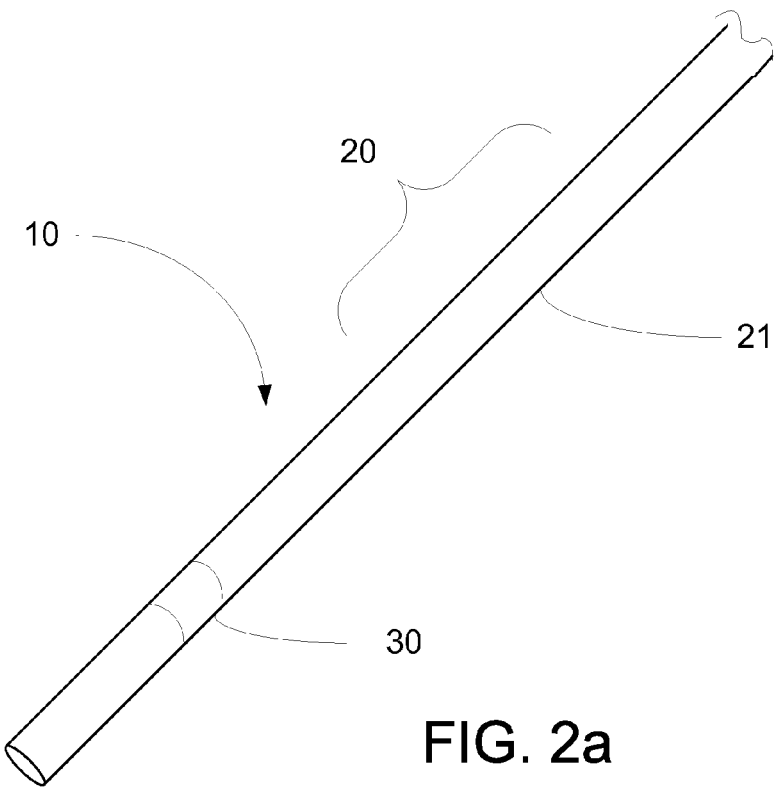
FIG. 2A is an exemplary embodiment of a portion of a lead in accordance with the invention while being exposed to a first temperature.
Figure 2B:
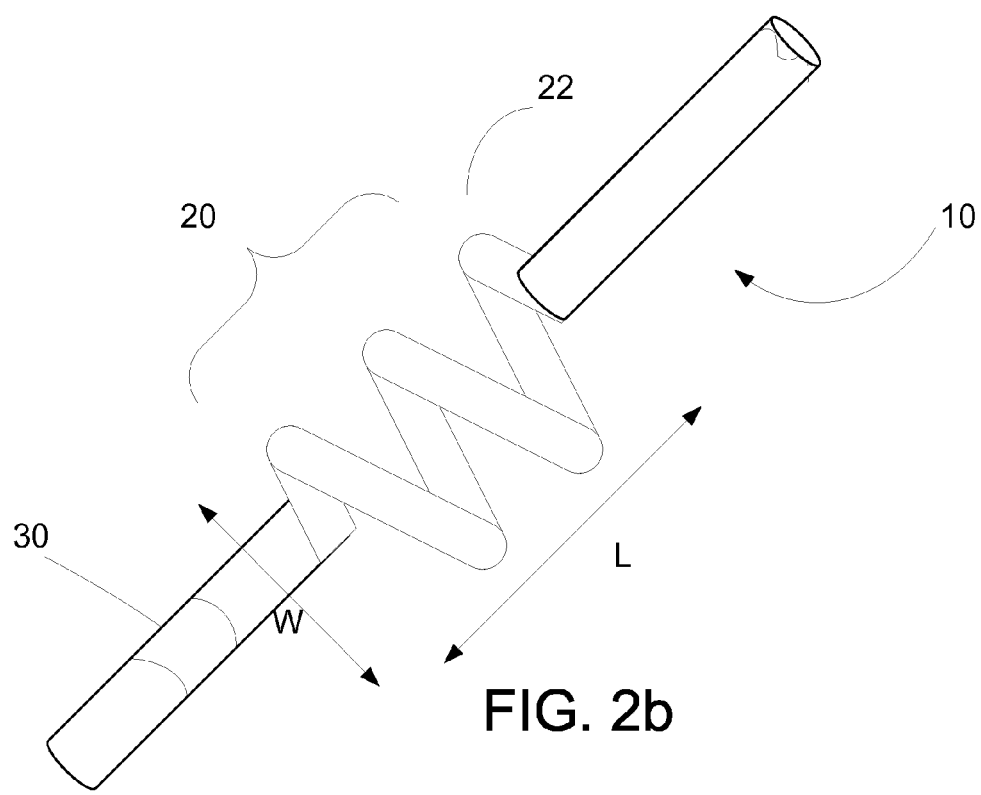
FIG. 2B is an exemplary embodiment of a portion of a lead in accordance with the invention while being exposed to a second temperature.

FIGS. 2A and 2B offer an example of a lead 10 while exposed to a first temperature (FIG. 2A) and while exposed to a second temperature (FIG. 2B). As seen there, the modifiable portion 20 goes from a substantially straight configuration 21 to a spiral or helical configuration 22. In one embodiment a helical configuration may provide advantages because it may provide fixative capabilities and strain relief. The strain relief may be able to accommodate any sudden, large displacement of the lead by absorbing the forces in the "spring" like helical structure.

In an embodiment of a lead in accordance with the invention that includes a helical second configuration that is designed to be used for stimulation within the pelvic region, the helical configuration can generally have a length L (as shown in FIG. 2B) from about 5 mm to about 25 mm. In another embodiment, the length L of the helical configuration is from about 10 mm to about 20 mm. In yet another embodiment the length L of the helical configuration is about 13 mm to about 17 mm. One of skill in the art will understand that different lengths L could be utilized depending on both the type of tissue that the lead is to be fixated in and the anatomy of the surrounding location of implantation.

In an embodiment of a lead in accordance with the invention that includes a helical second configuration that is designed to be used for stimulation within the pelvic region, the helical configuration can generally have a width W (as shown in FIG. 2B) from about 3 mm to about 20 mm. In another embodiment, the width W of the helical configuration is from about 6 mm to about 12 mm. In yet another embodiment the width W of the helical second configuration is about 8 mm to about 10 mm.

Embodiments of the invention can also have a width W that varies over the length L of the second helical configuration. In one embodiment the width W can be greater at the distal end (distal end is the end of the second helical configuration that is closest to the distal tip of the lead) than it is at the proximal end of the second helical configuration, for example. In one embodiment of the invention, the most distal edge of the helical second configuration could have a smaller coil diameter. Such an embodiment may allow the coil of the second helical configuration to form gradually, which may be less likely to change the proximity of the electrodes to the nerve. One of skill in the art will understand that different widths W could be utilized depending on both the type of tissue that the lead is to be fixated in and the anatomy of the surrounding location of implantation.

In one embodiment of the invention that is designed to be used for implantation within the pelvic floor for sacral nerve stimulation, the lead may be configured so that the second configuration lies in close proximity to the foramen after the lead is implanted. In another embodiment of the invention that is designed to be used for implantation within the pelvic floor for sacral nerve stimulation, the lead may be configured so that the second configuration forms within the foramen. Such a lead could allow the second configuration to act against the bone and the inside of the foramen, or on either side of the facial layer covering the foramen to further anchor the lead where it is implanted.

Figure 3A:
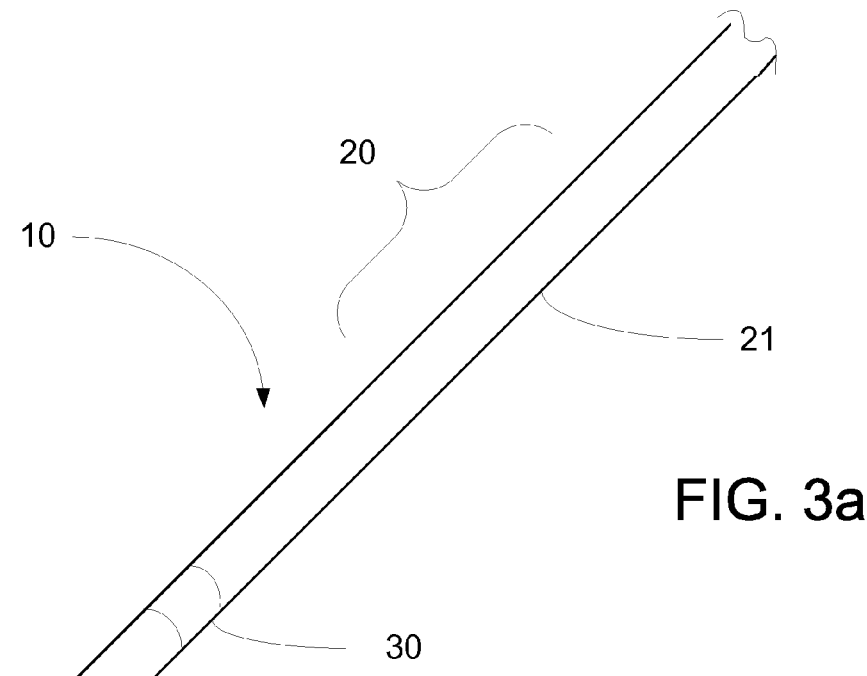
FIG. 3A is an exemplary embodiment of a portion of a lead in accordance with the invention while being exposed to a first temperature.
Figure 3B:
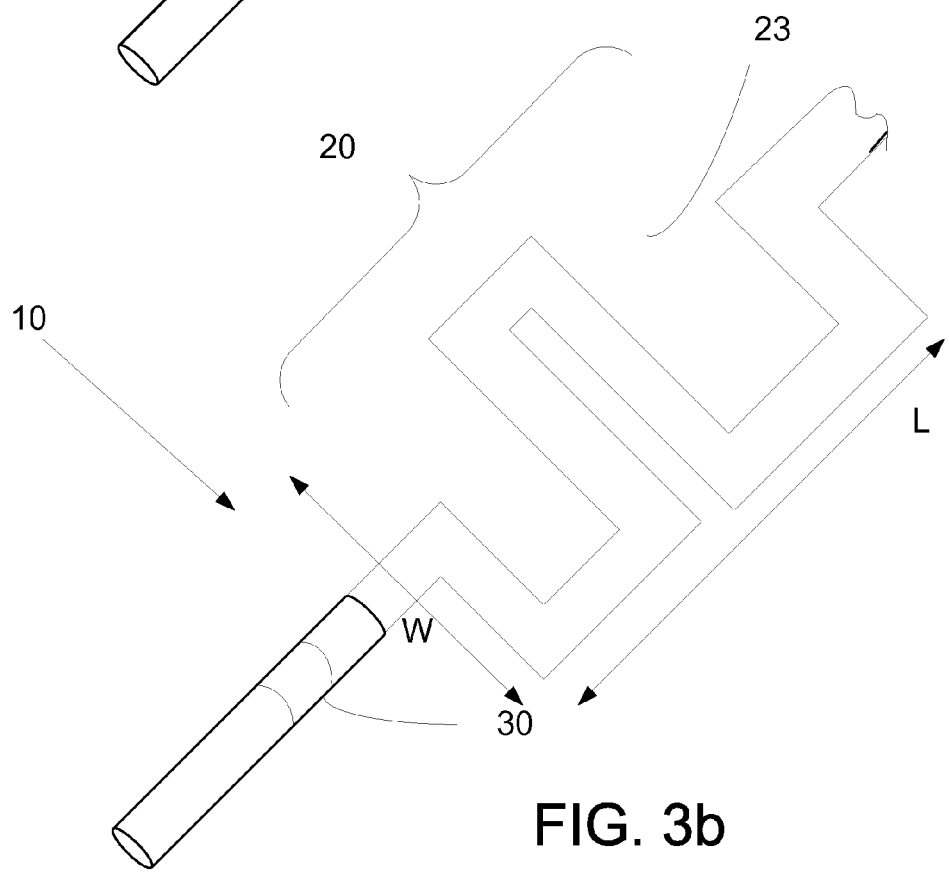
FIG. 3B is an exemplary embodiment of a portion of a lead in accordance with the invention while being exposed to a second temperature.

FIGS. 3A and 3B offer another example of a lead 10 while exposed to a first temperature (FIG. 3A) and while exposed to a second temperature (FIG. 3B). As seen there, the modifiable portion goes from a substantially straight configuration 21 to a stepped configuration 23 such as a square wave or a more rounded configuration having a more sigmoid shape (similar to a sine wave). In one embodiment a stepped configuration could form its shape at the facial layer that covers the foramen. In such an embodiment, the step in the lead could form a right angle distal to the puncture through the facia, which could provide excellent tensile resistance from pulls on the lead body that would normally dislodge the lead.

In an embodiment of a lead in accordance with the invention that includes a stepped second configuration that is designed to be used for stimulation within the pelvic region, the stepped configuration can generally have a length L (as shown in FIG. 3B) from about 5 mm to about 30 mm. In another embodiment, the length L of the stepped configuration is from about 10 mm to about 20 mm. In yet another embodiment the length L of the stepped second configuration is about 13 to about 17 mm. One of skill in the art will understand that different lengths L could be utilized depending on both the type of tissue that the lead is to be fixated in and the anatomy of the surrounding location of implantation.

In an embodiment of a lead in accordance with the invention that includes a stepped second configuration that is designed to be used for stimulation within the pelvic region, the stepped configuration can generally have a width W (as shown in FIG. 3B) from about 3 mm to about 20 mm. In another embodiment, the width W of the stepped configuration is from about 6 mm to about 12 mm. In yet another embodiment the width W of the stepped second configuration is about 8 mm to about 10 mm. Embodiments of the invention can also have a width W that varies over the length L of the second stepped configuration. In one embodiment the width W can be greater at the distal end (distal end is the end of the second stepped configuration that is closest to the distal tip of the lead) than it is at the proximal end of the second stepped configuration, for example. One of skill in the art will understand that different widths W could be utilized depending on both the type of tissue that the lead is to be fixated in and the anatomy of the surrounding location of implantation.

Figure 4A:
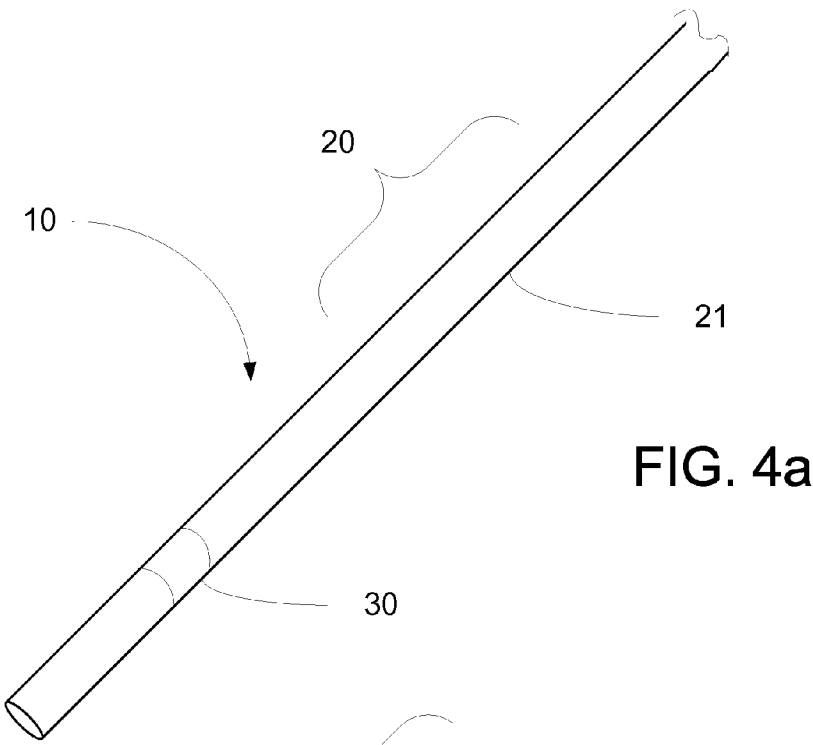
FIG. 4A is an exemplary embodiment of a portion of a lead in accordance with the invention while being exposed to a first temperature.
Figure 4B:
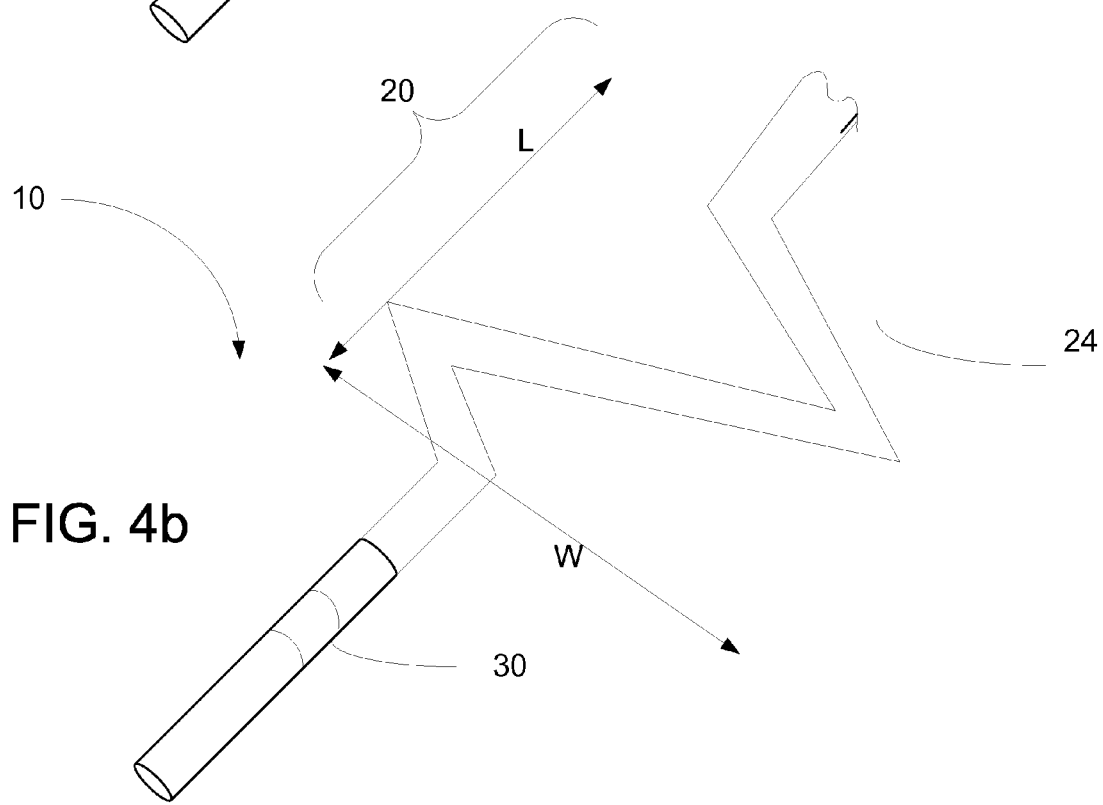
FIG. 4B is an exemplary embodiment of a portion of a lead in accordance with the invention while being exposed to a second temperature.

FIGS. 4A and 4B offer another example of a lead 10 while exposed to a first temperature (FIG. 4A) and while exposed to a second temperature (FIG. 4B). As seen there, the modifiable portion goes from a substantially straight configuration 21 to a zigzag configuration 24 (similar to a sawtooth waveform). In one embodiment a zigzag configuration could provide with a more pointed geometry at the width excursions could provide more burrowing ability into the surrounding tissue. That may allow more pressure to be exerted at the tip of the width features and thereby provide the desired strain relief and fixation.

In an embodiment of a lead in accordance with the invention that includes a zigzag second configuration that is designed to be used for stimulation within the pelvic region, the zigzag configuration can generally have a length L (as shown in FIG. 4B) from about 5 mm to about 30 mm. In another embodiment, the length L of the zigzag configuration is from about 10 mm to about 20 mm. In yet another embodiment the length L of the zigzag second configuration is about 13 mm to about 17 mm. One of skill in the art will understand that different lengths L could be utilized depending on both the type of tissue that the lead is to be fixated in and the anatomy of the surrounding location of implantation.

In an embodiment of a lead in accordance with the invention that includes a zigzag second configuration that is designed to be used for stimulation within the pelvic region, the zigzag configuration can generally have a width W (as shown in FIG. 4B) from about 3 mm to about 20 mm. In another embodiment, the width W of the zigzag configuration is from about 6 mm to about 12 mm. In yet another embodiment the width W of the zigzag second configuration is about 8 mm to about 10 mm. Embodiments of the invention can also have a width W that varies over the length L of the second zigzag configuration. In one embodiment the width W can be greater at the distal end (distal end is the end of the second zigzag configuration that is closest to the distal tip of the lead) than it is at the proximal end of the second zigzag configuration, for example. One of skill in the art will understand that different widths W could be utilized depending on both the type of tissue that the lead is to be fixated in and the anatomy of the surrounding location of implantation.

In one embodiment having a zigzag configuration, the point to point distance Z (on FIG. 4B) can also be modified based on factors such as the type of tissue that the lead is to be fixated in and the anatomy of the surrounding location of implantation. In one embodiment of the invention, the point to point distance Z can range from about 2 mm to about 6 mm.

One of skill in the art, having read this specification, will also understand that the at least one modifiable portion 20 of a lead 10 in accordance with the invention could have other types of second configurations. The second configuration provides a greater resistance to movement of the lead 10 within the body tissue than does the first configuration. Geometric second configurations that cause a greater resistance to movement of the lead 10 within the body tissue that were not exemplified herein are also included in the scope of this invention.

Figure 5:
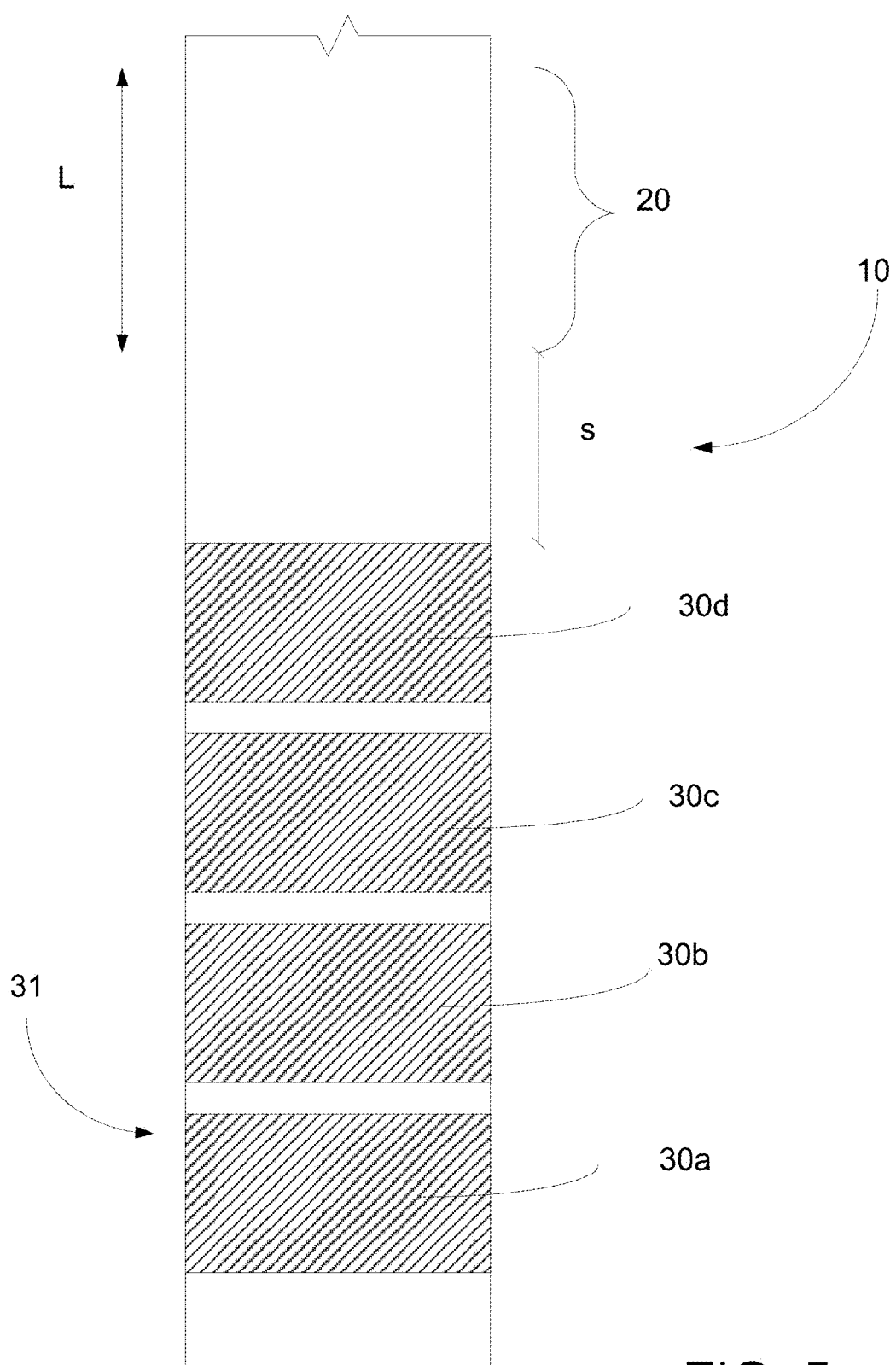
FIG. 5 is a diagram illustrating a portion of a lead in accordance with the invention.

FIG. 5 depicts another exemplary embodiment of a lead 10 in accordance with the invention. As seen in FIG. 5, a lead 10 in accordance with the invention has a spacer distance s between the modifiable portion and the most proximal electrode. In leads having more than one modifiable portion, the spacer distance s between the most proximal electrode and the first modifiable portion and the spacer distance s between the first modifiable portion and the second modifiable portion need not, but can be the same. One of skill in the art, having read this specification, will understand that whether or not the spacer distances s are the same, can depend at least in part on considerations such as, the type of tissue that the lead is to be implanted in, the surrounding anatomy where the lead will be implanted, the particular configuration of the second configuration of the modifiable portion, the number of modifiable portions within the lead, and the location of the at least one modifiable portion within the lead.

In one embodiment, spacer distance s can range from about 1 mm to about 20 mm. In another embodiment, spacer distance s can range from about 5 to about 15 mm. In yet another embodiment, spacer distance s is about 10 mm. One of skill in the art, having read this specification, will understand that any particular spacer distance s can vary depending at least in part on considerations such as, the type of tissue that the lead is to be implanted in, the surrounding anatomy where the lead will be implanted, the particular configuration of the second configuration of the modifiable portion, the number of modifiable portions within the lead if there is more than one, and the location of the one or more modifiable portions within the lead.

As described above, a lead 10 may include at least one modifiable region 20 to fix the lead in any tissue surrounding the lead, such as tissue within an epidural region or tissue within or near a foramen 14 of sacrum 16 for example. At least one modifiable region 20 may be located between electrodes 30 at a distal end of lead 10, or at a proximal end of lead 10. In one embodiment, at least one modifiable region 20 may be disposed proximal to the electrode 30 near the distal end 31 of lead 10 in order to fix the electrodes in place relative to a target stimulation site. In one embodiment, a lead in accordance with the invention may have more than one modifiable region 20. In one embodiment of the invention, a lead of the invention may have 1, 2, 3, 4, or more modifiable regions.

As discussed above, a lead in accordance with the invention has at least one modifiable portion that has a first configuration when exposed to a first temperature and a second configuration when exposed to a second temperature that is higher than the first temperature. In one embodiment of the invention, the second temperature is a temperature that is above an average ambient room temperature and the first temperature is a temperature that is below an average room temperature. In another embodiment, the second temperature is at or above an average body temperature and the first temperature is at or below an average body temperature. As used herein, "average body temperature" generally refers to the body temperature of a patient whom a lead of the invention is being implanted into. In one embodiment and average body temperature is one between about 97 and about 100 degrees Fahrenheit (or about 36 to about 38 degrees Celsius). In another embodiment an average body temperature is between about 98 to about 99 degrees Fahrenheit (or about 37 degrees Celsius).

When manufacturing a lead in accordance with this invention, the lead body, including the one or more electrode(s), the one or more modifiable portion(s), and any other features of the lead can be manufactured as was known to one of skill in the art, having read this specification, at the time of the invention.

Figure 6:
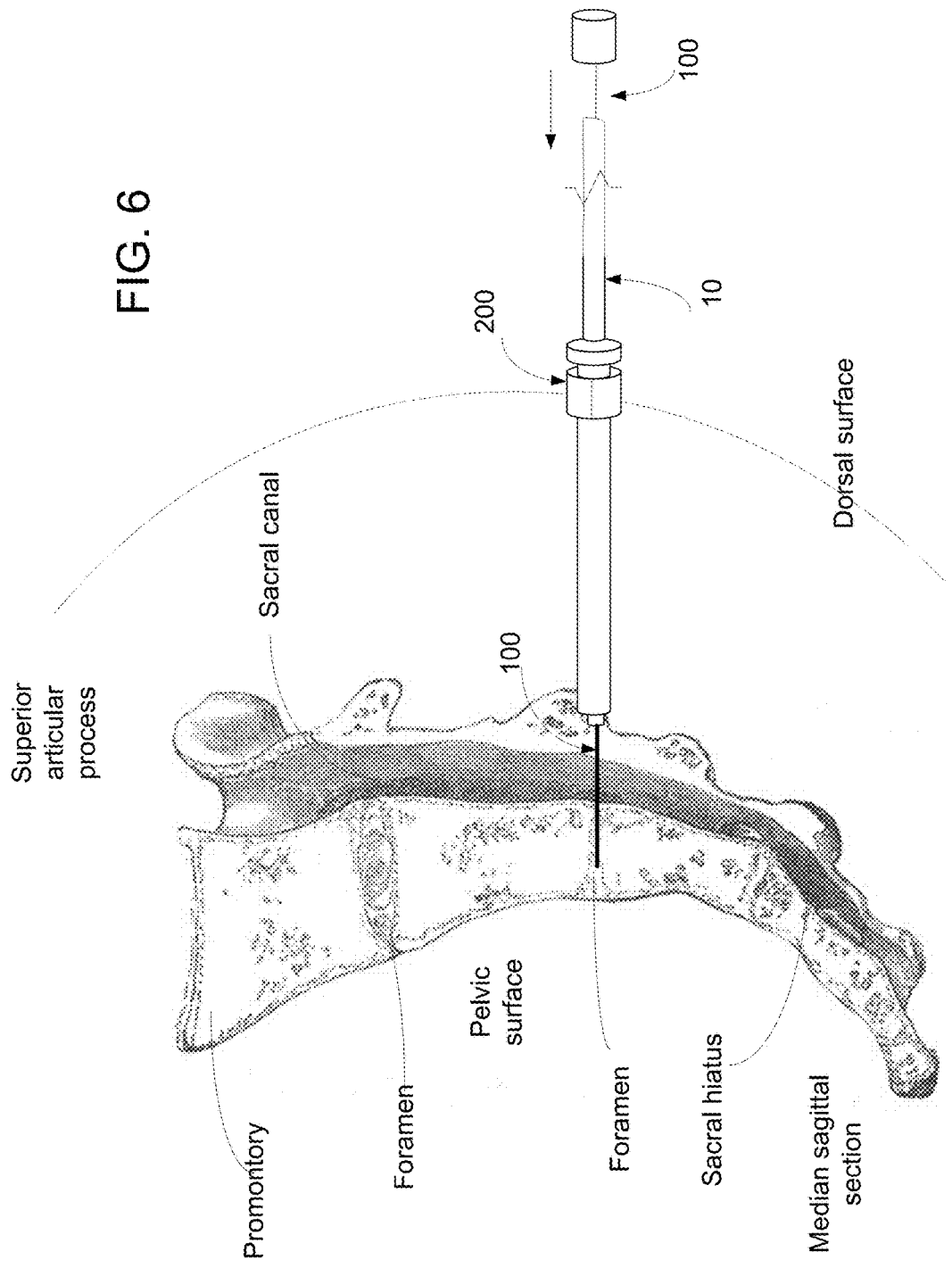
FIG. 6 is a cross-section view of the sacrum schematically illustrating an initial step of implanting a lead of the invention with the modifiable portion of the lead exposed to a first temperature.

FIGS. 6-9 depict the primary steps of implanting the sacral nerve stimulation lead 10 of the invention. An introducer 200 receives the distal portion 31 of the lead including the at least one electrode 30 and the at least one modifiable portion disposed within the lumen of the introducer 200. A stylet 100 can be disposed within the lead body lumen so that its distal tip closes the lumen distal end opening. The assembly can be advanced percutaneously at a selected angle until the introducer distal end is disposed at the selected foramen as shown in FIG. 6.

To determine the best location of the one or more electrodes, an insulated needle with both ends exposed for electrical stimulation can be used to locate the foramen and locate the sacral nerve by applying electrical stimulation through the needle using an external pulse generator. The efficacy of the location is tested by evaluating the physiologic response in relation to the electrical threshold energy required to elicit the response. For control of urinary incontinence, the physician can implant the medical electrical lead 10 near the S3 sacral nerves. The implantable medical electrical lead 10 may, however, be inserted near any of the sacral nerves including the S1, S2, S3, or S4, sacral nerves accessed via the corresponding foramen depending on the necessary or desired physiologic response.

The advancement of the introducer 200 can be accomplished separately over a guide wire previously percutaneously advanced from the skin incision into the foramen to establish the angle of advancement. Also, a two-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately provides the introducer 200 in the location depicted in FIG. 6.

The lead 10, optionally stiffened by the stiffening stylet 100 disposed in the lead lumen, is advanced through the introducer lumen proximal end opening into the introducer lumen. However it is accomplished, the at least one electrode 30 and the at least one modifiable portion 20 are disposed within the introducer lumen pre-positioned to be implanted in relation to the sacral nerve accessed through the foramen and in the subcutaneous tissue, respectively.

Figure 7:
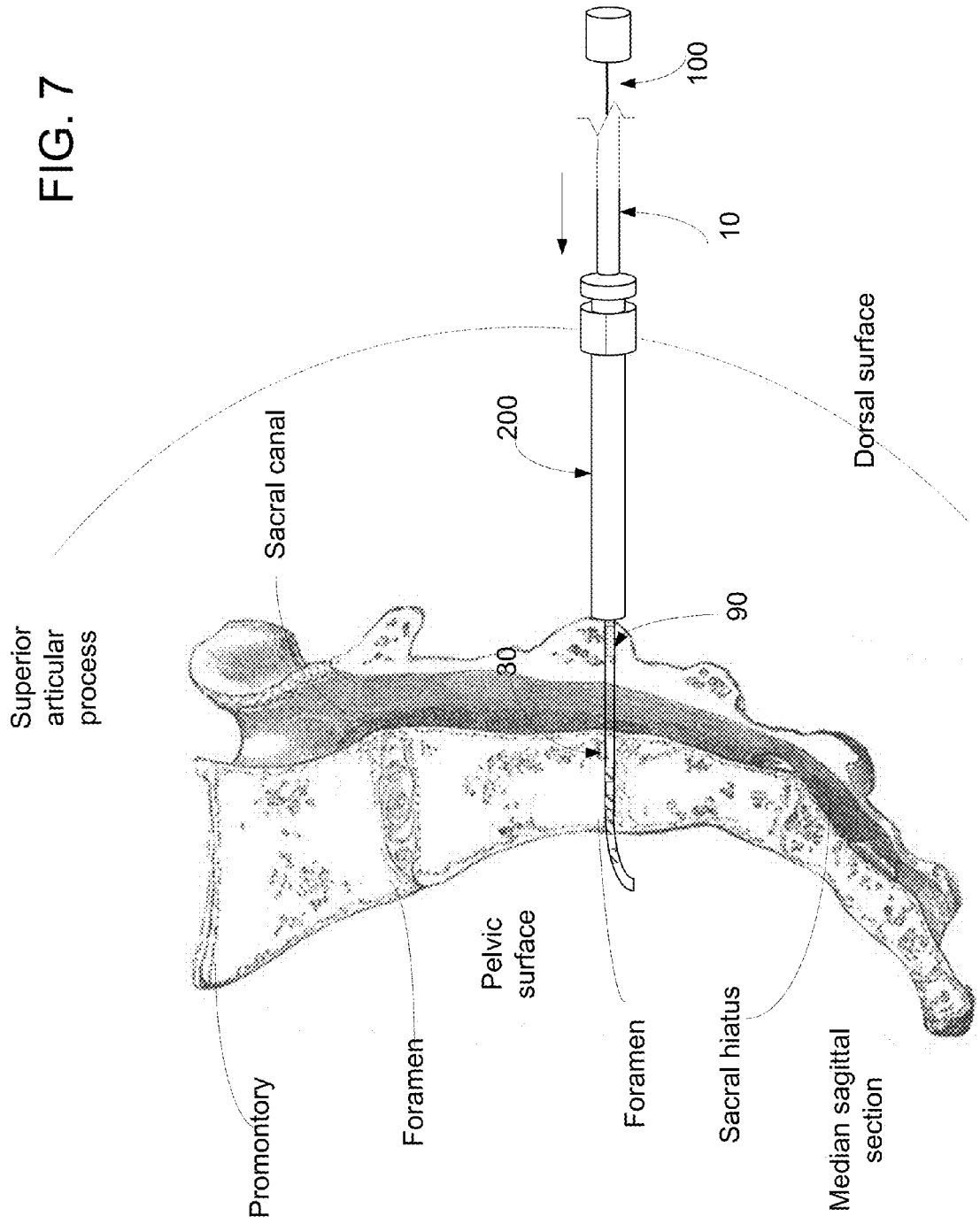
FIG. 7 is a cross-section view of the sacrum schematically illustrating a further step of implanting a lead of the invention extending the one or more electrodes through a foramen.

The stylet 100 may be advanced distally through the foramen as depicted in FIG. 6 or the lead 10 and the stylet wire 100 can both be advanced distally out of the introducer lumen distal end opening to advance the at least one electrode 30 into or through the foramen from the posterior entrance into casual contact with the more anterior sacral nerve as shown in FIG. 7.

Figure 8:
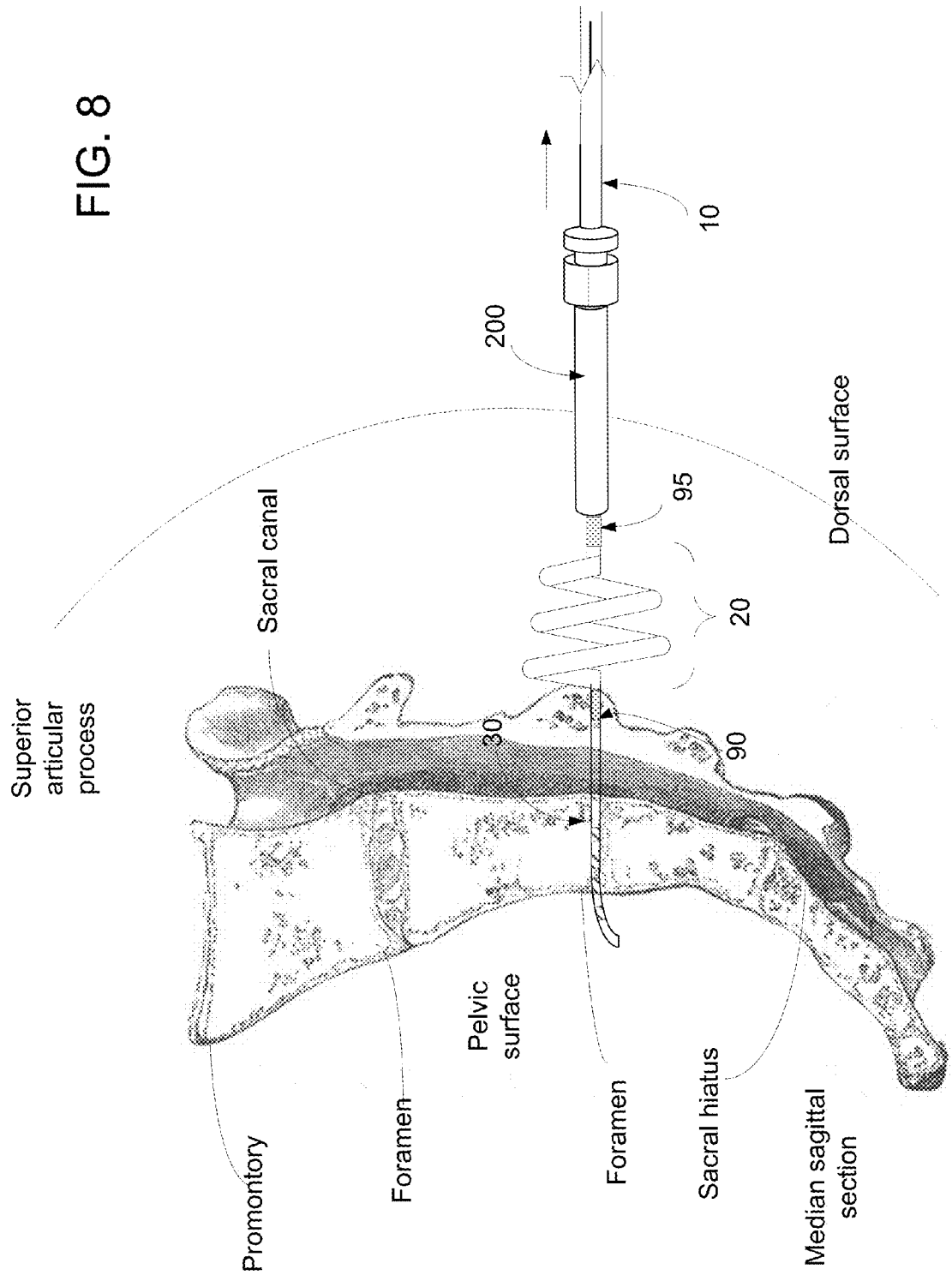
FIG. 8 is a cross-section view of the sacrum schematically illustrating a further step of implanting a lead of the invention retracting the introducer and after the modifiable portion was exposed to a second temperature.

After electrical testing to establish optimal positioning is completed the introducer 200 is retracted proximally. The at least one modifiable portion 20 is now exposed to the body temperature of the patient. This exposure causes the modifiable portion 20 to transition to its second configuration as shown in FIG. 8. In one embodiment, the first temperature can be lower than an average room temperature. In such an embodiment, the lead can be cooled to well below the second temperature before it is implanted. In one embodiment where the lead is cooled to a temperature well below the second temperature, the introducer (which is discussed below with respect to methods of implanting a lead of the invention) can function to insulate the cooled lead and increase the time before the lead reaches the second temperature. In a further embodiment, the lead is flushed with chilled saline to ensure that the first configuration is maintained, and then the temperature of the body tissue causes it to transition to its second configuration. In another embodiment, the lead can be made to more quickly take on its second configuration by heating the area around the modifiable portion once the lead is deployed from the introducer. In yet another embodiment, the lead is allowed to take on its second configuration as the body tissue of the patient warms the lead to the second temperature.

The introducer 200 and lead stylet 100, if present, are completely removed in FIG. 8. As shown in FIG. 9, the proximal portion 55 of the lead 10 is bent laterally with respect to the distal portion of the lead 10 and implanted through a subcutaneously tunneled path to the neurostimulator IPG.

In one embodiment of the invention, a lead 10 can include one or more markers, of which marker 90 is an example. Such markers can be made of materials that can be visualized under fluoroscopy. This can allow the physician to more easily see where the particular parts of the lead 10 are within the patient. For example, a lead that has a first marker 90 on the distal end of a modifiable portion 20 and a second marker 95 (as seen in FIGS. 8 and 9) on the proximal end of the modifiable portion, can allow the position of the modifiable portion 20 to be easily located within the patient. When the modifiable portion 20 transitions into the second configuration, it bears against the tissue and inhibits proximal retraction of the lead body through the subcutaneous tissue if traction is applied to the lead body since the second configuration resists inversion, migration, retraction, and displacement in the proximal direction. Leads in accordance with the invention can also provide strain relief between proximal forces (or strains) in the lead body and the desired location of the electrodes.

The medical electrical leads and procedures of the present invention can be used to stimulate multiple nerves or multiple sides of a single nerve bundle. It should also be understood that although sacral nerve stimulation was exemplified herein, the leads of the invention can be used for other types of nerve stimulation. In addition, the medical electrical lead 10 can also be used as an intramuscular lead where the at least one modifiable portion can engage against muscle and assist in preventing dislodgement of the at least one electrode. This may be useful in muscle stimulation such as dynamic gracilo-plasty or stomach stimulation for gastroparesis or obesity.

Although the invention has been described in detail with particular reference to a certain embodiments thereof, it will be understood variations and modifications can be effected within the scope of the following claims. Such modifications may include substituting elements or components which perform substantially the same function in substantially the same way to achieve substantially the same result for those described herein.

We claim:

1. An implantable medical electrical lead for electrical stimulation of body tissue comprising:
 at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and
 at least two electrodes configured to provide electrical stimulation of body tissue,
 wherein the lead has a proximal end and a distal end, wherein one of the at least two electrodes is a most proximal electrode on the lead, wherein the modifiable portion is disposed proximal to the most proximal electrode, and wherein the distance between the most proximal electrode and the at least one modifiable portion, referred to as a spacer distance, s, is from about 2 mm to about 30 mm.

2. The lead according to claim 1, wherein the at least one modifiable portion is made of Nitinol.

3. The lead according to claim 2, wherein the Nitinol has from about 55% to about 56% nickel and about 44% to about 45% titanium.

4. The lead according to claim 2, wherein the Nitinol has about 55.6% nickel and about 44.4% titanium.

5. The lead according to claim 1, wherein the second temperature is above an average ambient temperature.

6. The lead according to claim 1, wherein the second temperature is between about 36 and about 38 degrees Celsius.

7. The lead according to claim 2, wherein the Nitinol has a transition temperature between about 20 and about 40 degrees Celsius.

8. The lead according to claim 2, wherein the Nitinol has a transition temperature between about 25 and about 37 degrees Celsius.

9. The lead according to claim 2, wherein the Nitinol has a transition temperature between about 30 and about 37 degrees Celsius.

10. The lead according to claim 2, wherein the Nitinol has a transition temperature of about 30 degrees Celsius.

11. The lead according to claim 1, wherein the second configuration is a helical configuration.

12. The lead according to claim 1, wherein the second configuration is a stepped configuration.

13. The lead according to claim 1, wherein the second configuration is a zigzag configuration.

14. The lead according to claim 1, wherein the lead has at least four electrodes.

15. The lead according to claim 1, wherein the spacer distance is from about 5 mm to about 15 mm.

16. The lead according to claim 1, wherein there is two or more modifiable portions.

17. The system according to claim 1, wherein the spacer distance is from about 5 mm to about 15 mm.

18. The lead according to claim 1, wherein at least two electrodes are located towards the distal end of the lead.

19. A medical electrical stimulation system comprising:
an implantable pulse generator for providing medical electrical stimulation; and
a medical electrical lead coupled to the implantable pulse generator for electrical stimulation of body tissue, the medical electrical lead comprising at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and
at least two electrodes configured to provide electrical stimulation of body tissue,
wherein the lead has a proximal end and a distal end, wherein one of the at least two electrodes is a most proximal electrode on the lead, wherein the modifiable portion is disposed proximal to the most proximal electrode, and wherein the distance between the most proximal electrode and the at least one modifiable portion, referred to as a spacer distance, s, is from about 2 mm to about 30 mm.

20. The system according to claim 19, wherein the at least one modifiable portion is made of Nitinol.

21. The system according to claim 20, wherein the Nitinol has from about 55% to about 56% nickel and about 44% to about 45% titanium.

22. The system according to claim 20, wherein the Nitinol has about 55.6% nickel and about 44.4% titanium.

23. The system according to claim 19, wherein the second temperature is above an average ambient temperature.

24. The system according to claim 19, wherein the second temperature is between about 36 and about 38 degrees Celsius.

25. The system according to claim 20, wherein the Nitinol has a transition temperature between about 20 and about 40 degrees Celsius.

26. The system according to claim 20, wherein the Nitinol has a transition temperature between about 25 and about 37 degrees Celsius.

27. The system according to claim 20, wherein the Nitinol has a transition temperature between about 30 and about 37 degrees Celsius.

28. The system according to claim 20, wherein the Nitinol has a transition temperature of about 30 degrees Celsius.

29. The system according to claim 19, wherein the second configuration is a helical configuration.

30. The system according to claim 19, wherein the second configuration is a stepped configuration.

31. The system according to claim 19, wherein the second configuration is a zigzag configuration.

32. The system according to claim 19, wherein the lead has at least four electrodes.

33. The system according to claim 19, wherein there is two or more modifiable portions.

34. The system according to claim 19, wherein at least two electrodes are located towards the distal end of the lead.

35. A method of providing electrical stimulation of body tissue at a stimulation site employing an implantable pulse generator comprising:
providing an implantable medical lead comprising:
a lead body extending between lead proximal and distal ends;
at least one modifiable portion that exhibits a first configuration when exposed to a first temperature and a second configuration when exposed to a second temperature, wherein the second configuration of the modifiable portion exhibits a greater resistance to movement of the lead within the body tissue than does the first configuration, and the second temperature is higher than the first temperature; and
at least two electrodes configured to provide electrical stimulation of body tissue, wherein one of the at least two electrodes is a most proximal electrode on the lead,
wherein the at least one modifiable portion is disposed proximal to the most proximal electrode, and wherein the distance between the most proximal electrode and the at least one modifiable portion, referred to as a spacer distance, s, is from about 2 mm to about 30 mm;
at least one proximal connector element formed in a connector array in a proximal segment of the lead body;
percutaneously introducing the implantable medical lead adjacent to the stimulation site;
exposing at least the modifiable portion of the lead to the temperature of the body tissue; and
coupling the at least one proximal connector element with the implantable pulse generator.

36. The method according to claim 35 further comprising the step of using an insulated needle with both ends exposed to apply electrical stimulation through the needle using an external pulse generator in order to determine the best location for the at least one electrode.

37. The method according to claim 35 further comprising the step of testing the efficacy of the location.

38. The method according to claim 37, wherein the step of testing the efficacy of the location is accomplished by evaluating the physiologic response in relation to the electrical threshold energy required to elicit the response.

39. The method according to claim 36 further comprising the step of cooling the lead with chilled saline until after the step of claim 36 is completed.

40. The method according to claim 35 further comprising heating the body tissue with warm saline.

41. The method according to claim 35, wherein at least two electrodes are located towards the distal end of the lead.

* * * * *